United States Patent
Chan et al.

(10) Patent No.: US 8,313,481 B2
(45) Date of Patent: *Nov. 20, 2012

(54) APPARATUS AND METHOD FOR ADJUSTABLE FRACTIONAL OPTICAL DERMATOLOGICAL TREATMENT

(75) Inventors: Kin F. Chan, San Jose, CA (US);
George Frangineas, Freemont, CA (US); David Dewey, Mountain View, CA (US); Leonard C. Debenedictis, Palo Alto, CA (US)

(73) Assignee: Reliant Technologies, Inc., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/955,396

(22) Filed: Nov. 29, 2010

(65) Prior Publication Data
US 2011/0098691 A1  Apr. 28, 2011

Related U.S. Application Data

(63) Continuation of application No. 11/778,012, filed on Jul. 13, 2007, now Pat. No. 7,862,555.

(60) Provisional application No. 60/807,341, filed on Jul. 13, 2006, provisional application No. 60/939,088, filed on May 20, 2007.

(51) Int. Cl.
*A61B 18/20* (2006.01)
(52) U.S. Cl. .................... 606/9; 606/3; 606/10; 606/17; 607/88; 607/89
(58) Field of Classification Search ............. 606/3, 9–18; 607/88–91; 128/898
See application file for complete search history.

(56) References Cited

U.S. PATENT DOCUMENTS

| 7,938,821 B2* | 5/2011 | Chan et al. ...................... 606/9 |
| 2003/0216719 A1* | 11/2003 | Debenedictis et al. ......... 606/10 |
| 2005/0278002 A1 | 12/2005 | Eimerl et al. |
| 2008/0234669 A1 | 9/2008 | Kauvar |
| 2010/0082019 A1 | 4/2010 | Neev |
| 2010/0145321 A1* | 6/2010 | Altshuler et al. ................. 606/9 |

OTHER PUBLICATIONS

USPTO, Office Action issued in related U.S. Appl. No. 12/955,405 dated Oct. 14, 2011.
USPTO, Notice of Allowance issued in related U.S. Appl. No. 12/955,405 dated Jul. 13, 2012.

* cited by examiner

*Primary Examiner* — Ahmed Farah
(74) *Attorney, Agent, or Firm* — Wood, Herron & Evans, LLP

(57) ABSTRACT

In a fractional treatment system, an adjustable mechanism can be used to adjust the beam shape, beam numerical aperture, beam focus depth, and/or beam size to affect the treatment depth and or the character of the resulting lesions. Adjustment of these parameters can improve the efficiency and efficacy of treatment. Illustrative examples of adjustable mechanisms include a set of spacers of different lengths, a rotatable turret with lens elements of different focal distances, an optical zoom lens, and a mechanical adjustment apparatus for adjusting the spacing between two optical lens elements. In one aspect, the fractional treatment is configured with a laser wavelength that is selected such that absorption of the laser wavelength within the tissue decreases as the tissue is heated by the laser (e.g., 1480-1640 nm). Desirably, the laser wavelength is primarily absorbed within a treated region of skin by water and has a thermally adjusted absorption coefficient within the range of about 7 cm$^{-1}$ to about 26 cm$^{-1}$.

12 Claims, 14 Drawing Sheets

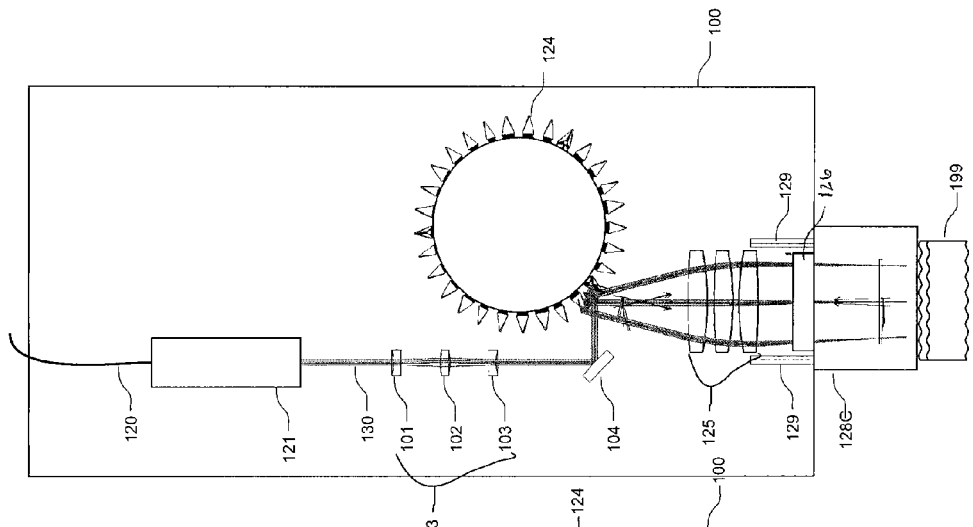
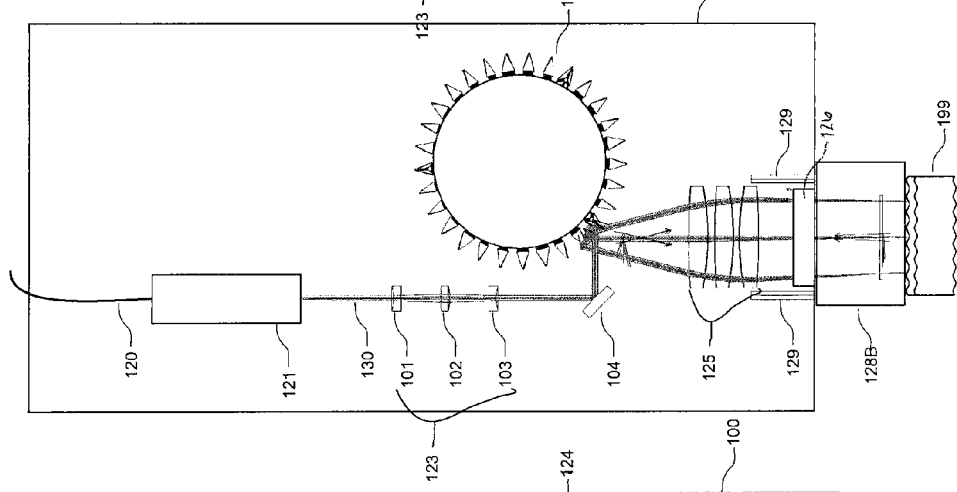
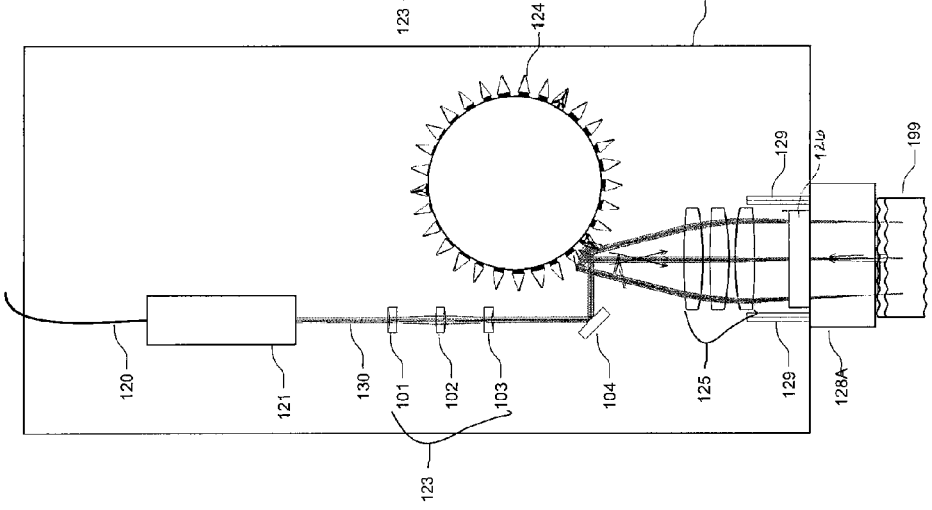
FIG. 2C
FIG. 2B
FIG. 2A

APPARATUS AND METHOD FOR ADJUSTABLE FRACTIONAL OPTICAL DERMATOLOGICAL TREATMENT

CROSS-REFERENCE TO RELATED APPLICATION

This application is a continuation of application Ser. No. 11/778,012, filed Jul. 13, 2007, which claims priority under 35 U.S.C. §119(e) to U.S. Provisional Application No. 60/807,341, "Apparatus and method for adjustable fractional optical dermatological treatment," by Kin F. Chan and Leonard C. DeBenedictis, filed Jul. 13, 2006; and claims priority under 35 U.S.C. §119(e) to U.S. Provisional Application No. 60/939,088, "Apparatus and method for adjustable fractional optical dermatological treatment," by Kin F. Chan, George Frangineas, Leonard C. DeBenedictis, and David Dewey, filed May 20, 2007. The subject matter of all of the foregoing is incorporated herein by reference in their entirety.

BACKGROUND

The present invention relates generally to methods and apparatus for providing medical or surgical treatment using optical energy, and in particular to a method and apparatus for providing cosmetic and noncosmetic fractional treatment of tissue (e.g., skin) using optical radiation.

Lasers can be used for cosmetic and noncosmetic treatment of tissue. For example, lasers are used in cosmetic dermatological procedures, such as skin resurfacing (including treatment of wrinkles), removal of pigmented lesions, treatment of vascular lesions, treatment of acne, treatment of acne scars, treatment of striae, etc.

The side effect profile of a dermatological laser treatment depends on a number of factors, such as the percentage of a skin area that is treated, the size of the treatment zones, shape of the treatment zone, and the character (e.g., ablative or nonablative, selective or nonselective, etc.) of the treatment that is delivered. Side effects can also result from variations within the patient population or the treatment environment. For example, the water content of a patient's skin can determine how deeply a water-absorbed wavelength of light penetrates into the skin. Other factors, such as the starting temperature of the skin and the temperature of the air can alter the effects of the laser on the skin and can affect the amount of pain perceived by the patient.

Fractional treatment can reduce some side effects relative to bulk treatment for a given level of treatment efficacy. The reduction in side effects is due in part to the improvement in predictability of the skin response that is possible with fractional treatment. Fractional treatment with a water-absorbed wavelength, for example, typically treats with very high local fluences that could not be tolerated in a bulk treatment. Skin can tolerate very high local fluences because tissue adjacent to each microscopic treatment region is spared and participates in the healing response of the wounded tissue. In fractional treatments, overtreatment and undertreatment typically results in a change in the size and shape of the lesion, but not a change in whether or not lesions occur. On the other hand, for bulk treatments, overtreatment may result in a lesion that scars an entire region of skin, while undertreatment may result in no lesion at all. Thus, through the use of very high local fluences, fractional treatments can reliably denature a desired portion of each illuminated region. Small variations in fractional treatment fluence or treatment conditions have less effect than corresponding variations would have in bulk treatment because fractional treatments can still reliably create clinically visible effects even if undertreated or overtreated.

Despite being more controlled than bulk treatments, fractional treatments still have unacceptable side effects that could be reduced by a device with improved control of lesion characteristics. For example, the side effect profile for many treatments is closely related to the percentage of cells at the dermal-epidermal junction ("DE junction") of a tissue portion that are killed during treatment. For this reason, it can be desirable to limit the percentage of treated tissue in a region. However, the treatment coverage percentage is also related to treatment efficacy in many treatment types. To achieve the desired efficacy while maintaining an acceptable side effect risk profile, it is desirable to have good control over the lesion dimensional characteristics, such as treatment zone width and depth.

In other fractional treatments, the side effect profile is stongly dependent on the distance to healthy tissue in the plane of the DE junction. Cells at the DE junction that are adjacent to treatment zones help to repair the damage created by the laser at the treatment zone and the time required for repairing treatment zones is strongly dependent on the size and shape of the treatment zone at the DE junction. For this reason, it is frequently desirable to create treatment zones with a small lesion width.

Treatment efficacy can be improved in many cases by reaching deeper tissue within the skin. This is particularly true, for example, when treating dermal scar tissue that frequently comprises scar tissue deep within the reticular dermis. In order to have short healing times and deep treatment zones, treatment zones with large aspect ratios are desirable for certain conditions. To control the diameter of the lesion at the DE junction and the depth of treatment, it is beneficial to have control over the treatment zone characteristics.

Another example where control over lesion characteristics would yield improved treatment results is in controlling the character of the treatment zones. For example, some fractional treatments are desirably not semiablative in order to reduce the duration and intensity of downtime and associated wound care following fractional laser treatment. If there is no reason to promote the disruption of epidermal layers, then it is desirable to maintain an intact epidermis to avoid an increased risk of infection, such as through creation of an open wound. On the other hand, for some treatments, it is desirable for the treatment to be semi-ablative. For example, a semi-ablative treatment can allow permeation of topically applied substances that promote the healing of the treated tissue. Existing laser treatment systems typically provide treatment that is either semi-ablative or not semi-ablative and do not have the capability of switching modes between semi-ablative and non-semi-ablative fractional treatments. A system with such capability is desirable so that two systems do not need to be purchased to accomplish these two goals.

Thus, there is a need for a fractional optical treatment system that allows for improved and adjustable control over fractional lesion characteristics, such as treatment zone width and depth, treatment zone aspect ratio, and/or the degree of disruptiveness of microscopic treatment zones.

SUMMARY OF THE INVENTION

The present invention overcomes many of the limitations of the prior art by increasing control over selected characteristics of fractional treatment zones. In one aspect, the inventive system comprises a fractional treatment system configured with a laser wavelength that is selected such that absorption of the laser wavelength within the tissue decreases as the tissue is heated by the laser. Preferably, the laser wavelength is primarily absorbed within a treated region of skin by water and has certain additional characteristics as described in the following paragraphs.

In some embodiments of the invention, an adjustable lens group and/or discretely interchangeable optical elements are employed in a fractional treatment system. The adjustable lens group and/or discretely interchangeable optical elements can be used to adjust the fractional pattern according to the desired treatment parameters by varying the spot size at the surface of the skin, the focal depth of the optical beam below the surface of the skin, the numerical aperture of the optical beam as it enters the skin, and/or the beam cross-sectional shape at the surface of the skin. The variations in optical parameters can be performed manually or by electronic control.

In some embodiments, the absorption of the laser wavelength in water is selected with specific characteristics. The laser wavelength can be selected, for example, such that the absorption of the laser wavelength for water is described by one or more of the following characteristics: (1) the thermally adjusted absorption coefficient is within the range of about 7 cm.sup.−1 to about 26 cm.sup.−1 or within the range of about 7 $cm^{-1}$ to about 12 $cm^{-1}$; and (2) the absorption of the laser wavelength in water decreases by at least 12% as the temperature of water is increased from 30° C. to 80° C., decreases by about 12% to about 20% as the temperature of water is increased from 30° C. to 80° C., or decreases by about 15% to about 20% as the temperature of water is increased from 30° C. to 80° C.

In some embodiments of the invention, the laser wavelength is in the range of about 1480 nm to about 1640 nm. In some embodiments of the invention, the laser wavelength is in the range of about 1560 nm to about 1640 nm. In some embodiments of the invention, the laser wavelength is about 1550 nm.

In some embodiments, the fractional optical treatment system comprises an adjustment mechanism that adjusts the spot size of the optical pulse at the skin surface. In some embodiments, this adjustment mechanism adjusts the spot size automatically. For example, given a pulse energy, the adjustment mechanism may automatically adjust the spot size and/or focus depth (see next paragraph) to maximize the depth of the resulting lesion for the given pulse energy.

In conventional systems, the distance from a reference plane corresponding approximately to the contact surface of the optical system with the skin to the optical focus in air along the direction of propagation of the optical treatment beam (i.e., the focus depth) may be selected as roughly equal to the depth of the desired lesion. However, in some embodiments of the invention, the selected focus depth is not approximately equal to the lesion depth. Rather, the adjustment mechanism adjusts the focus of the beam such that the focus depth is greater than twice the depth of the deepest portion of a lesion. In an alternate approach, the adjustment mechanism may adjust the focus so that the focus depth is less than one half of the depth of the lesion or such that the focus depth is negative (i.e., the optical focus of the optical beam is located outside the skin).

In some embodiments of the invention, a fiber laser is used, for example a Raman-shifted ytterbium-doped fiber laser, an erbium doped fiber laser, or a Raman-shifted erbium doped fiber laser. Other lasers can be used in other embodiments, such as diode lasers or diode lasers pumping erbium-doped fiber amplifiers.

Other aspects of the invention include methods corresponding to the systems described above, and applications of these systems and methods.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 1A and 1B are side views. FIG. 1C is a perspective view.

FIGS. 2A-2C are illustrations of the fractional treatment handpiece of FIG. 1A-1C depicting the use of an adjustable zoom lens in combination with a set of spacers of different lengths.

DEFINITIONS

For this patent application, the following terms are defined below.

The term "fractional treatment" describes a treatment comprising a series of treatment zones caused by a pattern of optical energy wherein the following condition is satisfied for a majority of the treatment zones: for each point within the treatment zone, the minimum lateral distance to a region of healthy tissue is approximately 0.5 mm or less and the treatment zone comprises a portion of the DE junction (i.e., comprises portions of dermal and epidermal tissue that were adjacent prior to treatment). For skin, such lateral distance measurements should be carried out in a 2-dimensional plane at the approximate depth of the DE junction. One example of a fractional treatment pattern is a discrete array of circular microscopic lesions, wherein each lesion has a diameter of approximately 1 mm (or less) and each lesion is adjacent to portions of healthy tissue. Another example of a fractional treatment pattern is a discrete array of lines of treatment where the width of each line is approximately 1 mm or less and the perimeter of each line is adjacent to portions of healthy tissue. In an ablative fractional treatment, the treatment zone includes the ablated region. So, for example, a 0.2 mm diameter ablated hole with a 0.2 mm coagulation region surrounding the ablated hole would be indicative of a fractional treatment. A 3 mm diameter ablated hole within a small ring of coagulation would not be indicative of fractional treatment.

The terms "laser wavelength," "laser diode wavelength," "wavelength of the laser," and similar variations describe the peak wavelength of the laser, for the wavelength band of interest.

The term "thermally adjusted absorption coefficient" for a wavelength of light means the average of the absorption coefficient for water at 30° C. and the absorption coefficient of water at 80° C. for the selected wavelength.

DETAILED DESCRIPTION OF THE PREFERRED EMBODIMENTS

A fractional treatment laser system that has variable lesion depths, widths, and aspect ratios for a preselected pulse energy can be created using an adjustable lens group and/or discretely interchangeable optical elements to adjust the optical beam numerical aperture or beam size at one or more epidermal layers. Such a laser system can be created by proper selection of laser beam parameters as described herein.

Figure 5B:
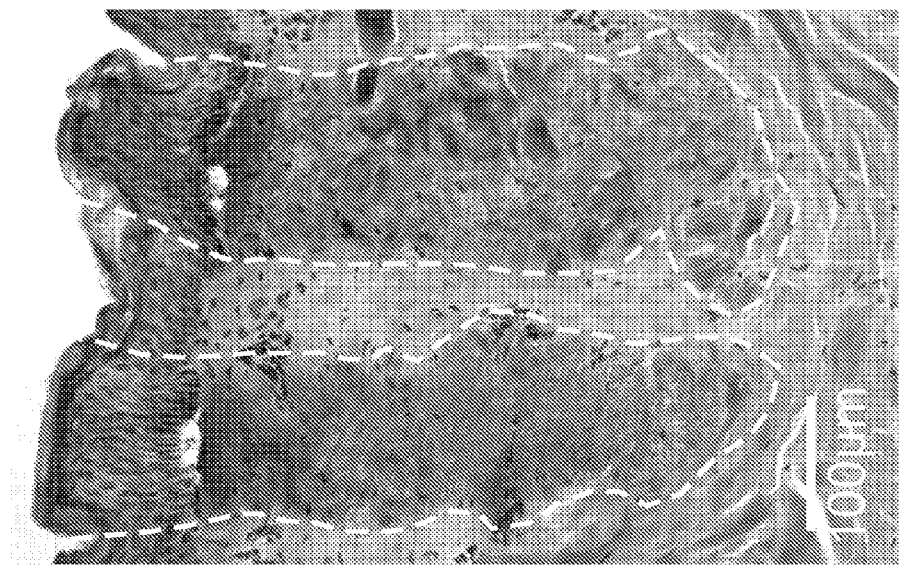
FIG. 5B shows a comparative histology of tissue treated according to an alternate method.
Figure 5A:
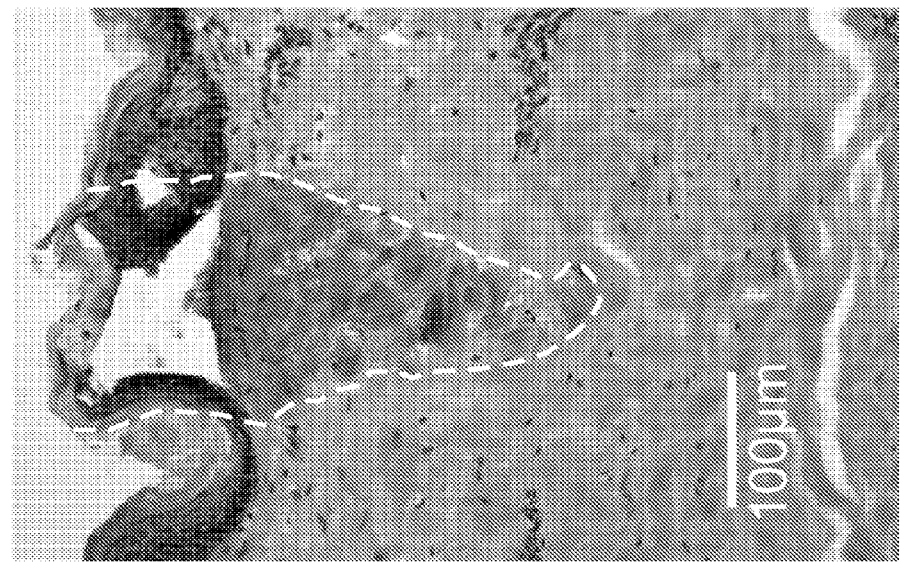
FIG. 5A shows a histological cross section of tissue treated according to an embodiment of the invention.

To demonstrate such a device, treatment zones were created by directing a laser beam onto ex vivo human skin that had been excised during one or more plastic surgery operations. Optical spot size and focus depth into the tissue sample were adjusted by adjusting the focal position of a focused laser beam relative to the tissue surface. The skin was frozen for storage and later warmed to body temperature before being treated. To approximate in vivo treatment conditions, treatment of the ex vivo tissue was performed at approximately body temperature while the sample was kept moist using saline solution. The skin was frozen and sectioned using standard histologic techniques. Staining was performed using hemotoxylin and eosin (H&E) stain to decorate features within the tissue. The results were then measured using a calibrated CCD camera mounted on a microscope. FIGS. 5A-B show sections of tissue sliced approximately perpendicular to the skin surface following laser treatments under selected exemplary conditions. The corresponding laser treatment parameters are given in Table 1.

TABLE 1

Laser beam treatment parameters for skin shown in FIGS. 5A-5B

| FIG. | Beam diameter at skin surface (to $1/e^2$ intensity point) | Treatment energy | Laser wavelength | Laser power |
|---|---|---|---|---|
| 5A | 180 μm | 10 mJ | 1410 nm | 4 W |
| 5B | 180 μm | 10 mJ | 1480 nm | 4 W |

The benefits of the decrease in absorption with temperature was demonstrated as shown in ex vivo treatments at 1410 nm and 1480 nm with comparable treatment parameters. The sliced sections of tissue in FIGS. 5A and 5B show the results of ex vivo treatment at these two wavelengths with other treatment parameters held constant (10 mJ of treatment energy per treatment zone using an approximately Gaussian beam with a spot size of 180 μm at the $1/e^2$ intensity point at the skin surface). Both treatments were performed using light delivered by single mode fiber from Raman-shifted fiber lasers. Raman shifted fiber lasers are available from IPG Photonics, Inc. (Oxford, Mass.).

At 30° C., the absorption of water is approximately the same for these two wavelengths, approximately 24 $cm^{-1}$ at 1410 nm and approximately 25 $cm^{-1}$ at 1480 nm. Despite having a slightly higher absorption at 30° C., the 1480 nm light penetrated deeper than the 1410 nm wavelength. The difference in penetration was partially due to a slight difference in scattering coefficient between these wavelengths, but the difference due to scattering is small in comparison to the difference due to the dynamic absorption characteristics of the water within the treatment zone. The difference in the depth of the treatment zones created with these two wavelengths was primarily due to the difference in absorption at temperatures above 30° C. since the tissue was locally heated significantly above 30° C. by the laser treatment, particularly in the upper layers of the tissue. As the skin was heated by the laser, the absorption coefficient changed due to the change in temperature. The microscopic treatment zone that resulted from treatment with the 1410 nm laser (FIG. 5A) is semiablative and has a shallower penetration than the microscopic treatment zone that resulted from treatment with the 1480 nm laser (FIG. 5B), which was not indicative of semi-ablative treatment. In each case, the lesions extend from the skin surface into the dermis.

The absorption of water for the 1410 nm wavelength increases monotonicly from 30° C. to 80° C. for a total increase over this range of approximately 22%. In contrast, the 1480 nm wavelength absorption is reduced monotonicly by approximately 15% over this same temperature range. The absorption trends with temperature for these two wavelengths continue monotonicly as water is heated to at least 100° C. For these reasons, despite having approximately the same absorption coefficient at 30° C., the resulting treatment lesions are very different in character and in depth.

In some embodiments of the invention, a handpiece is used to deliver laser light to a region of skin to be treated. The handpiece illustrated in FIG. 1A comprises an optical fiber 120 that delivers optical energy from a laser source 140. The end of the optical fiber 120 is mounted in an optical collimator unit 121 to collimate the optical beam 130 emitted from the optical fiber 120. The optical beam 130 is directed towards an adjustable lens group 123 that is comprised of three lens elements 101, 102, and 103. The individual lens elements can be adjusted using a motor 182. The optical beam 130 is reflected from an optional mirror 104 into the starburst scanner wheel 124. The starburst scanner wheel 124 deflects the optical beam 130 to the output lens group 125, which focuses the optical beam 130 through the output window 126 and into the skin 199. A spacer tip 128 is mechanically registered against reference pins 129 as an aid to preserving the desired distance between the output lens group 125 and the surface of the skin 199. The output lens group may be chosen to focus the optical beam at any desired location, either in the skin 199, at the surface of the skin 199, or above the surface of the skin 199. The spacer tip 128 may optionally comprise a transparent contact plate 127.

Handpiece 100 can be moved across the skin at a constant rate in a direction into and out of the page, while the starburst scanner wheel 124 is moved at a constant rate by a motor (not pictured). This can be used to create a fractional treatment with a desired pattern. More complicated velocity feedback systems such as those employing an optical mouse chip with a contrast enhancing agent applied to the skin can be used as described, for example, in copending patent application Ser. No. 11/020,648, "Method and Apparatus for Monitoring and Controlling Laser-Induced Tissue Treatment" and Ser. No.

11/468,275, "Method And Apparatus For Monitoring And Controlling Thermally Induced Tissue Treatment," both of which are herein incorporated by reference to provide additional flexibility.

The laser source 140 comprises one or more lasers. The laser wavelength can be in the range of 1350 nm to 2500 nm. In this range, the laser is primarily and substantially absorbed within the skin by water. Since water is distributed more uniformly than chromophores within the skin, this makes treatment with a wavelength that is primarily absorbed by water less selective. Use of such a wavelength will therefore produce a more reproducible treatment zone than if a wavelength is used that is not substantially absorbed by water or is dependent on the specific distribution of chromophores, such as melanin or blood, within the skin.

Suitable lasers can be made at many different wavelengths and can be made from many different technologies.

The laser wavelength can be selected to have a thermally adjusted absorption coefficient within the range of about 7 $cm^{-1}$ to about 26 $cm^{-1}$ or within the range of about 7 $cm^{-1}$ to about 12 $cm^{-1}$. Laser wavelengths that have a thermally adjusted absorption coefficient greater than about 26 $cm^{-1}$ do not typically penetrate deeply into the tissue to be treated. Laser wavelengths that have a thermally adjusted absorption coefficient less than about 7 $cm^{-1}$ require more laser energy to switch into semi-ablative mode and are therefore less desirable.

Laser wavelengths that have a thermally adjusted absorption coefficient within the range of about 7 $cm^{-1}$ to about 26 $cm^{-1}$ provide a useful treatment depth for fractional treatment applications. Lasers with wavelengths outside of these absorption ranges are also within the scope of the invention, particularly when coupled with other aspects of the invention, such as adjustable lens groups which can permit adjustment of the spot size of the treatment beams.

The thermally adjusted absorption coefficient of a fractional laser treatment system can be chosen based on the desired treatment effect. Wavelengths that are absorbed within the tissue primarily by water are useful for treatment of wrinkles, pigmented lesions, vascular lesions, etc. For such wavelengths, the water content of the skin is important. The dermal layer of skin typically contains approximately 70% water. For a wavelength that is absorbed in the tissue primarily by water, the penetration of the light into tissue depends primarily on the absorption coefficient of the laser wavelength in water. So, for example, light with an absorption coefficient of 27 $cm^{-1}$ in water has an absorption coefficient of about 19 $cm^{-1}$ in skin, and the delivered power of a treatment beam with this absorption will be reduced by about 63% (i.e., to its 1/e point) at a depth of 0.5 mm beneath the skin surface, assuming that scattering is negligible. The actual depth of the treatment zone will depend on the exact device configuration and skin characteristics. The treatment zone depth may be deeper or shallower than the penetration depth, but will be affected by the thermally adjusted absorption coefficient. For treatment beams with a small numerical aperture, the energy deposition at a desired treatment depth can be maximized by selecting the thermally adjusted absorption coefficient in skin as approximately the inverse of the desired maximum treatment depth. For treatments where the maximum lesion depth is about 0.5 to 2 mm, the wavelength of the treatment laser can be chosen such that the thermally adjusted absorption coefficient is within the range of about 7 $cm^{-1}$ to about 26 $cm^{-1}$ or within the range of about 8 $cm^{-1}$ to about 12 $cm^{-1}$.

Figure 3:
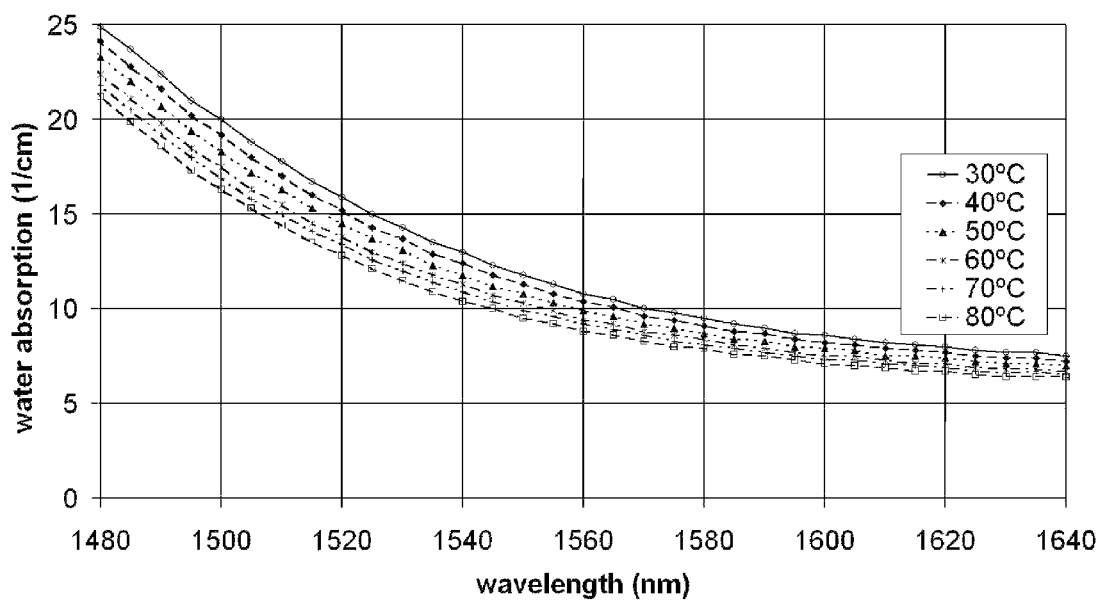
FIG. 3 is a graph showing the measured temperature dependence of the absorption spectrum of water over the temperature range of 30-80° C. for the wavelength range of 1480-1640 nm.

FIG. 3 shows measurements of the absorption spectrum for water as a function of wavelength as the temperature of water was changed from approximately 30° C. to approximately 80° C. These measurements were taken using transmission light spectroscopy, wherein light was transmitted through a heated sample of water. As the temperature of water was increased from 30° C. to 80° C., the absorption of light by water decreased for light with wavelengths in the range of about 1480 nm to about 1640 nm.

As described above, the thermally adjusted absorption coefficient can be used in selecting the maximum depth of penetration for a device. If a deeper lesion is desired, the efficiency with which a treatment zone can be created to a desired depth can be further improved by adjusting the average fluence on the skin in conjunction with a choice of wavelength that has an absorption that decreases dynamically as the temperature of the skin increases. For many treatments, the dynamic decrease in absorption can provide important benefits to the treatment response of the skin. Some of these benefits can be illustrated with an example: For a given pulse energy, say 10 mJ, concentrating the pulse energy into a beam with a small diameter, say 30-70 µm, creates a high intensity at the treatment region and thus rapidly heats the tissue and consequently rapidly adjusts the absorption coefficient of the tissue to enhance the depth of penetration. The energy in the treatment pulse is absorbed within a small depth and creates a less intense superficial local treatment effect than would occur without the dynamic change in absorption. This is useful in avoiding the creation of bubbles within the tissue that can scatter or reflect the beam to reduce the beam intensity below the upper portion of the treatment zone, which would limit the penetration of the optical treatment energy to deeper layers of tissue.

For an optical beam that is larger at the skin surface (and having the same energy, pulse duration, etc.), the rate of change in temperature at the skin surface is slower. Therefore, a larger percentage of the treatment energy can pass through the upper portions of the illuminated region when the illuminated region is at low temperature. Thus, theory would suggest that the treatment energy may not penetrate as deeply with the larger beam in comparison to the smaller beam, particularly when the absorption dynamically decreases with the temperature of the skin and/or of water within the skin. However, for the high fluences typically used in fractional treatments, scattering sites are created, for example, by the vaporization of water within the skin. For that reason, we have discovered that in order to maximize the penetration depth of a beam, it is advantageous to use a wavelength for which absorption decreases as and to use a larger beam size as the pulse energy increases for treatments with high local fluence.

Thus, the system can function as if it has an adjustable absorption source simply by varying optical beam parameters, such as focal position, numerical aperture, beam diameter, and beam shape. This can avoid a need for employing an expensive tunable source in certain laser treatment systems.

A laser wavelength that has an absorption that decreases in water with increasing temperature allows lower pulse energies to be used to create deep lesions where it is advantageous to have a lower absorption coefficient when dealing with high pulse energies and high local fluences. Such wavelengths also can be beneficially incorporated with appropriate optical design to increase the depth of coagulation and damage within the dermis to increase treatment efficacy for hair removal or for treatment of scars, wrinkles, melasma, and other dermatological conditions with significant dermal components. The laser wavelength can be chosen such that the absorption of the laser wavelength in water decreases by at least 12% as the temperature of water is increased from 30° C. to 80° C., decreases by about 12% to about 20% as the temperature of water is increased from 30° C. to 80° C., or decreases by about 15% to about 20% as the temperature of water is increased from 30° C. to 80° C.

Figure 4:
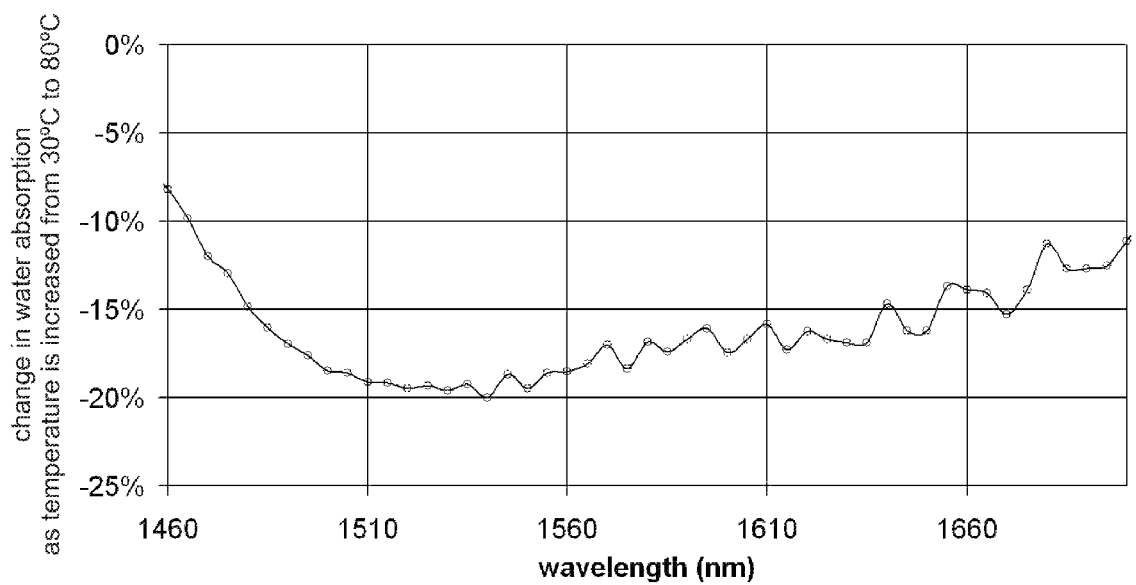
FIG. 4 is a graph showing the measured percentage difference in the absorption of water at 80° C. and absorption of water at 30° C. as a function of wavelength for the wavelength range of 1460-1700 nm.

The percentage change in absorption as water was heated from approximately 30° C. to approximately 80° C. is shown in FIG. 4. As mentioned earlier, the absorption of light by water decreases with temperature over the wavelength range of about 1480 nm to about 1640 nm. The measured percentage decrease in absorption was within the range of about 12% to about 20% in the wavelength range of about 1470 nm to about 1680 nm. In wavelength range of about 1480 nm to about 1640 nm, the decrease in absorption in water was within the range of about 15% to about 20%.

Given all of the factors described above, it can be desirable in many applications to operate a laser within the wavelength range of about 1480 nm to about 1640 nm, of about 1560 nm to about 1640 nm, or of about 1550 nm. Fiber lasers and Raman-shifted fiber lasers at these wavelengths are commonly available, such as from IPG Photonics, Inc. (Oxford, Mass.).

The laser source 140 comprises one or more lasers. For example, the laser source can comprise one or more fiber lasers. Fiber lasers are desirable because of their high beam quality, precisely controlled wavelength, lack of temperature dependence, and lack of mirrors to be aligned. In particular, erbium-doped glass fiber lasers can be used to produce wavelengths in the range of about 1520 to about 1620 nm.

As mentioned above, by choosing a laser wavelength for which the absorption decreases with temperature, the system can function as if it has an adjustable absorption source simply by varying optical beam parameters, such as focal position, numerical aperture, beam diameter, and beam shape. This can avoid a need for employing an expensive tunable source in certain laser treatment systems. For example, a single, fixed-wavelength fiber laser can be used in the laser source 140.

The adjustable lens group 123 can be adjusted during treatment or between treatments to create different optical treatment conditions resulting from changes in optical beam parameters, for example, changes in the spot size at the surface of the skin 199, the focal depth of the optical beam 130 below the surface of the skin 199, the numerical aperture of the optical beam 130 as it enters the skin 199, and or the beam cross-sectional shape at the surface of the skin 199. By adjusting the spot size, the optical treatment energy in the optical beam 130 can be concentrated or distributed to create a large or a small area of interaction between the tissue and the skin surface as desired. Small spots may create more disruption at the surface of the skin 199. These effects can be avoided to create deeper lesions by using a wavelength with a dynamically decreasing absorption, such as wavelengths in the range of about 1480 nm to about 1640 nm. With such wavelengths, if the optical beam 130 enters the skin with a small spot size, the temperature of the upper layers of the skin will be heated rapidly and their absorption will shift quickly, thus decreasing absorption and causing a decrease in the local damage caused by the treatment beam. If the beam is adjusted, such that the optical beam 130 enters the skin with a large spot size, the temperature of the upper layers of the skin will be heated more slowly and disruptive scattering sites can be reduced and the treatment beam will thus be able to penetrate more deeply. To maximize the lesion depth, there is a theoretical optimum, just below the point where scattering sites are created. In practice, it has been found that larger spot sizes are typically better for the high intensities used to create fractional treatments and that practical limits of the optics (e.g., numerical aperture of lenses) are typically reached before there is a significant drop off in pulse depth due to a large optical size. Thus, by adjusting the optical beam parameters, the beam 130 can increase the depth of a treatment lesion without needing to incorporate a second laser or a tunable laser.

The treatment modes that are not semi-ablative can be optimized to enhance the penetration depth of the treatment beam to more efficiently create treatment zones at the desired location in the skin 199 by reducing the dynamic heating in the upper layers of the skin. Various optical beam parameters can be used to vary the treatment effect of a treatment beam with dynamic absorption. For example, the use of high numerical aperture may be used to reduce or eliminate the need for cooling of the skin surface, for example, if sparing of epidermal tissue is desired.

Changing of the beam shape can be useful for minimizing the effects of visible patterns on the skin and for altering the thermal distribution within the skin to allow penetration of the beam while still maximizing concentration of the beam at a desired depth below the skin surface. For example, the beam may be adjusted to be more of a "flat top" shape at the skin surface to distribute the beam intensity over a larger area when deeper penetration is desired. If such a beam is then brought to a focus at the desired depth, then the heating at the desired depth can be maximized. The beam shape can alternatively be varied, for example, if one or more of lens elements 101, 102, 103 are chosen to be radially asymmetric such as for example a cylindrical element. Such radially asymmetric elements may optionally be rotated in addition to being adjusted in distance from one another in order to vary the treatment patterns. Other parameters that can be desirably varied using the inventive apparatus will be obvious to those skilled in the art.

The adjustable lens group 123 can be designed and assembled using techniques commonly employed for optical zoom lenses. For example, by appropriately adjusting the distance between two or more optical elements, the characteristics of the optical beam 130 can be adjusted.

In an embodiment, the optical spot size is focused at the skin surface for a spot size of less than approximately 90 μm. To achieve smaller spot sizes, lens elements 101 and 103 are each moved closer to lens element 102 along the optical axis. This increases the diameter of the optical beam 130 that is injected into the starburst scanner wheel 124. To achieve larger spot sizes at the surface of the skin 199, lens element 103 remains fixed and the distance between lens elements 101 and 102 is reduced as desired to move the focus of the beam into the skin 199. By moving the focus of the beam 130 into the skin 199, the diameter of the beam 130 at the surface of the skin 199 increases to distribute the optical energy over a larger area at the skin surface. Thus, the beam size and focus depth can be adjusted for the desired treatment.

Examples of ranges of appropriate optical lens design parameters are given in Table 2. Broader ranges of these parameters can be created by those skilled in the art. The specific optical design depends on the desired span for the beams, the number of spots created by the scanning wheel, the type of scanner used, the optical wavelength, and mechanical constraints of the design for the handpiece. The specific design can easily be optimized by those skilled in the art based on the constraints and desired performance for a particular system.

TABLE 2

Illustrative examples of lens design parameters

| | |
|---|---|
| Lens elements 101 and 103 | (−20)-(−15) mm focal length |
| Lens elements 102 | 10-15 mm focal length |
| Output lens group 125 | 20-50 mm focal length |
| Starburst scanner wheel 124 | diameter to outside of teeth = 40-60 mm number of teeth 15-50 |

Figure 1A:
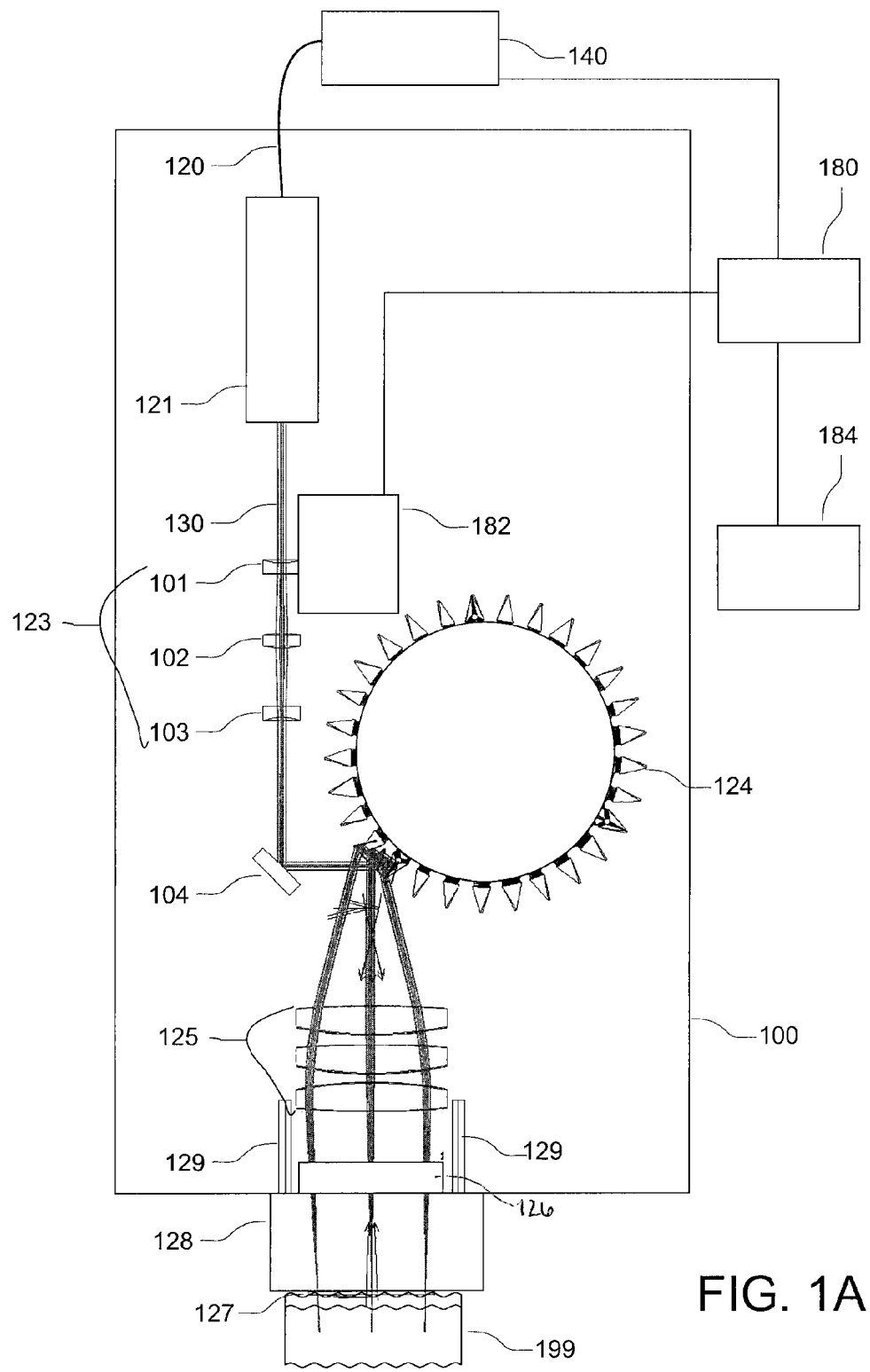
FIGS. 1A-1C are illustrations depicting different views of a fractional treatment handpiece incorporating an adjustable zoom lens and a spacer.
Figure 1B:
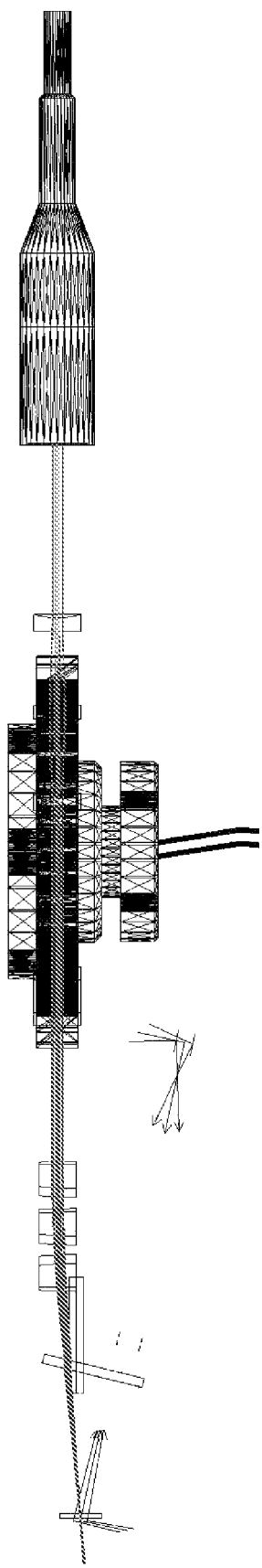
Figure 1C:
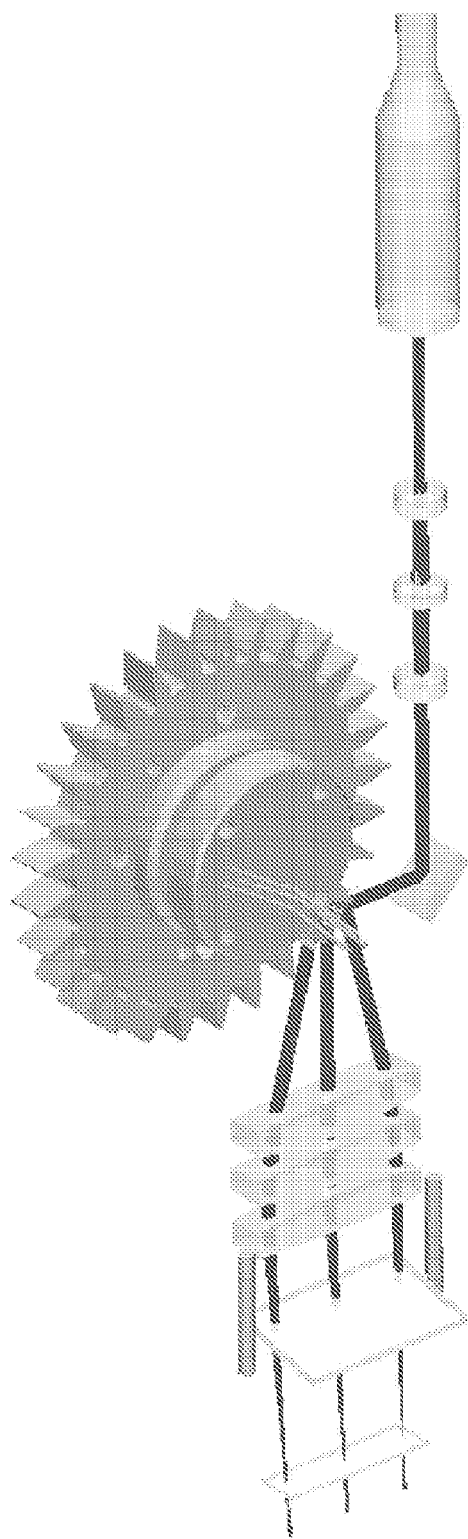

An example embodiment of the invention has been characterized using an erbium doped fiber laser emitting a wavelength of approximately 1550 nm as the optical source 140. The example embodiment was functionally similar to the embodiment shown in FIGS. 1A-C. With reference to FIGS. 1A-C, the lens elements 101 and 103 were adjusted along the optical axis with respect to lens element 102 to adjust simultaneously both the spot size at the surface of the skin 199 and the focus depth of the optical beam 130 in the skin 199. Ex vivo tissue was procured and process as explained for the FIGS. 5A and 5B described above. Histology slices were stained with hemotoxylin and eosin and were analyzed using a light microscope to estimate the dimensions of the coagulation created under the treatment conditions.

Figure 9:
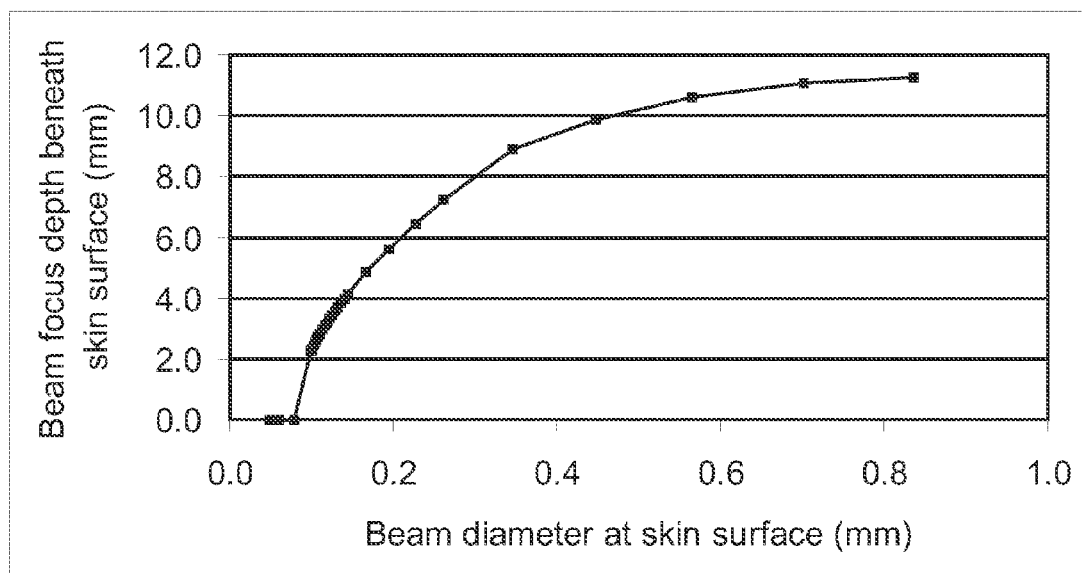
FIG. 9 is a graph showing the variation of spot size with focus depth according to the parameters used to generate the histology depicted in FIGS. 7 and 8A-8G.

FIG. 9 is a graph showing the variation of optical spot size with focus depth according to the parameters used to for the ex vivo treatments summarized in FIGS. 7 and 8A-8G. Note that for small focuses, the optical beam was focused at the skin surface for these experiments. Representative measurements were recorded and are plotted in FIGS. 7 and 8A-8G to show the variation of treatment depth and lesion shape, respectively, as the optical focus and optical spot size at the surface of the skin were varied. As can be seen from FIGS. 7 and 8A-8G, the deepest lesions for different pulse energies were achieved using different optical spot sizes at the skin surface. There was some effect on these results due to the adjustment of the focus depth affecting the convergence of the beam at depth. However, this effect is believed to be significantly smaller than the effect produced by the change in optical spot size at the skin surface and in the upper layers of the skin.

Figure 7:
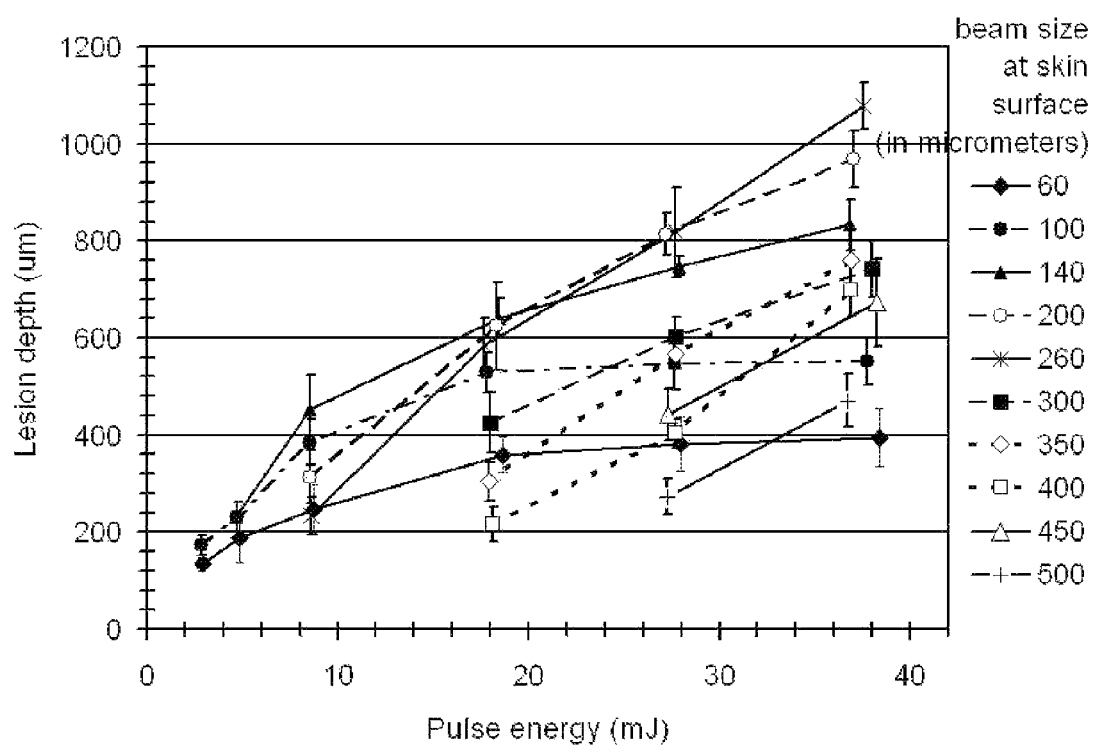
FIG. 7 is a graph showing the variation in treatment depth using the handpiece illustrated in FIGS. 1A-C as the optical focus depth and optical spot size at the surface of the tissue are varied.
Figure 8A:
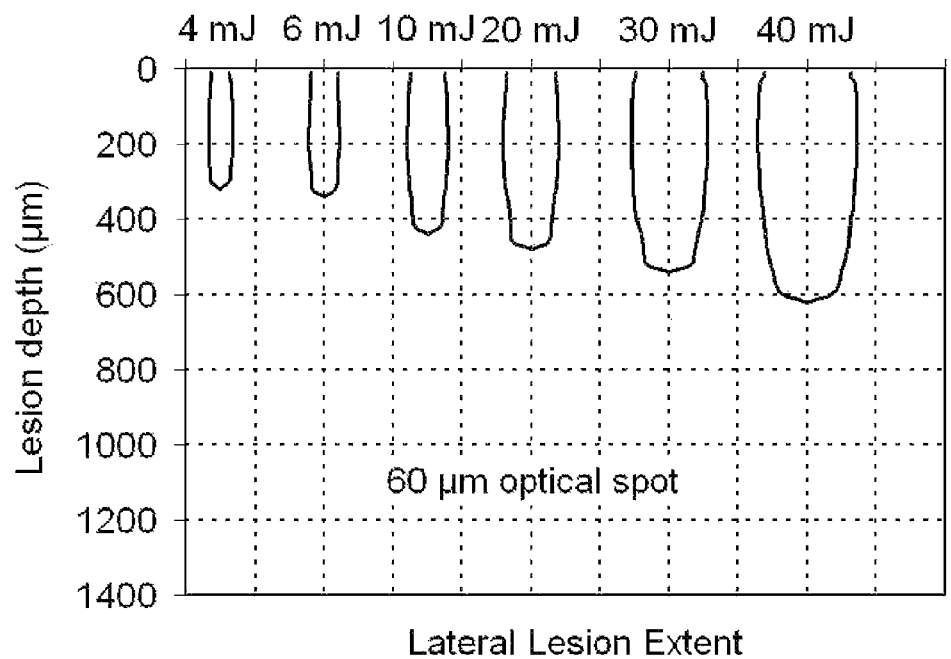
FIGS. 8A-8G are graphs showing the variation in treatment lesion dimensions and shape using the device illustrated in FIGS. 1A-C as the optical focus depth and optical spot size are varied for selected treatment energies.
Figure 8B:
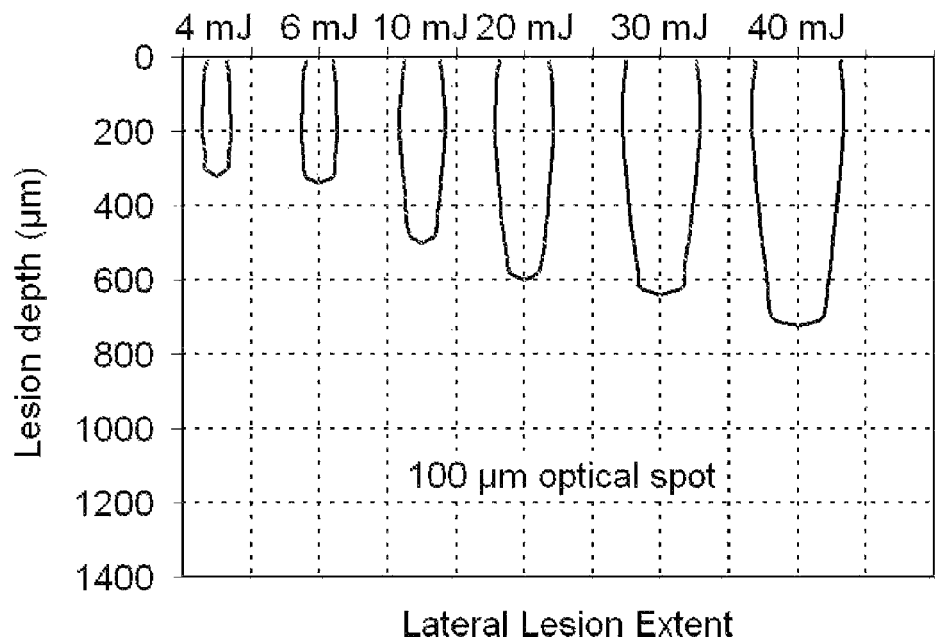
Figure 8C:
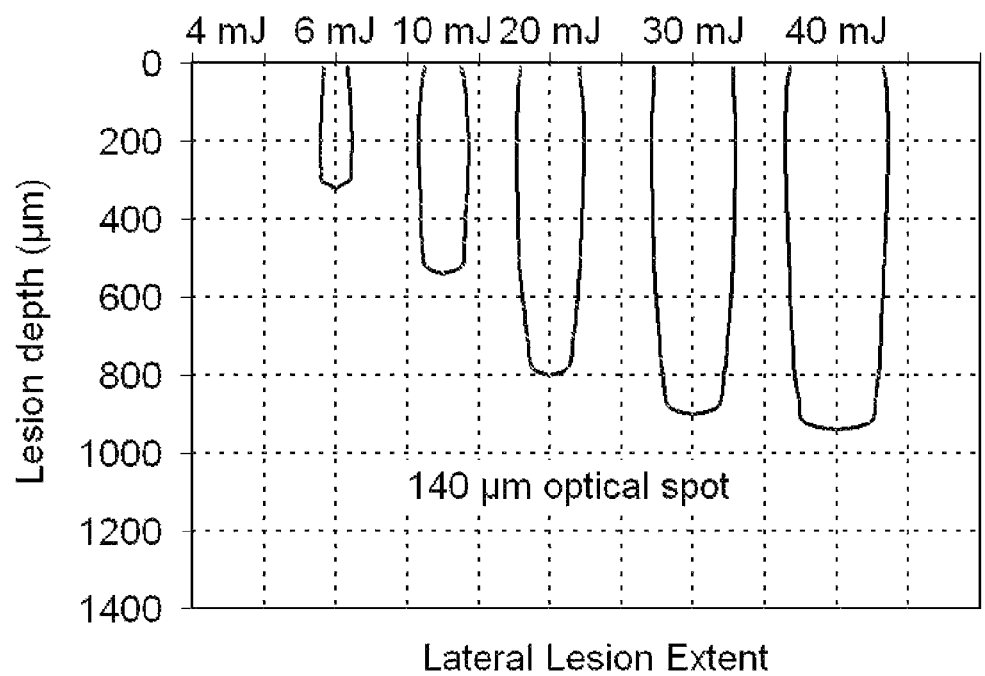
Figure 8D:
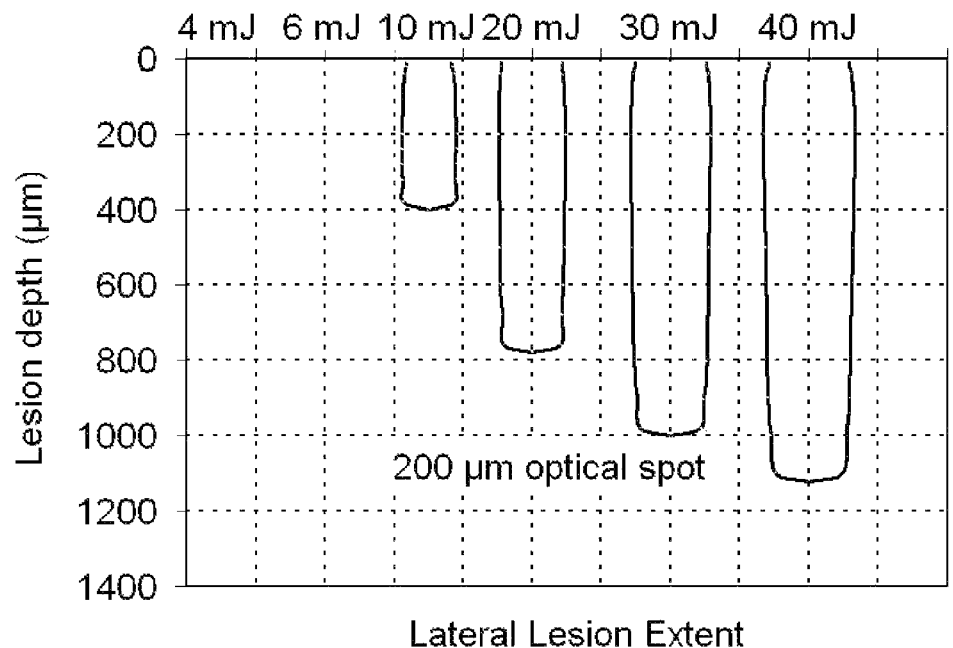
Figure 8E:
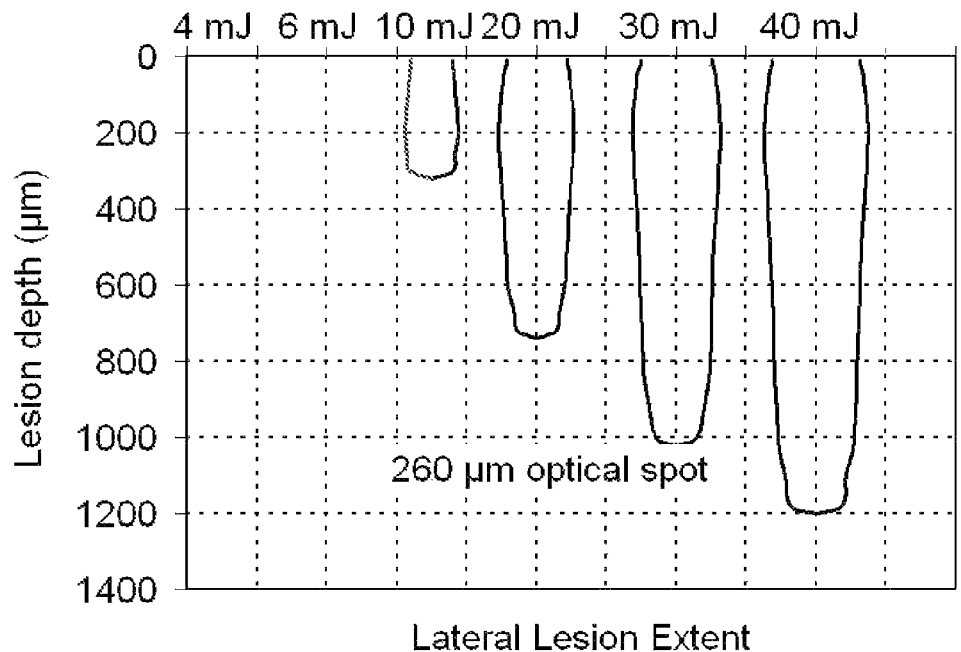
Figure 8F:
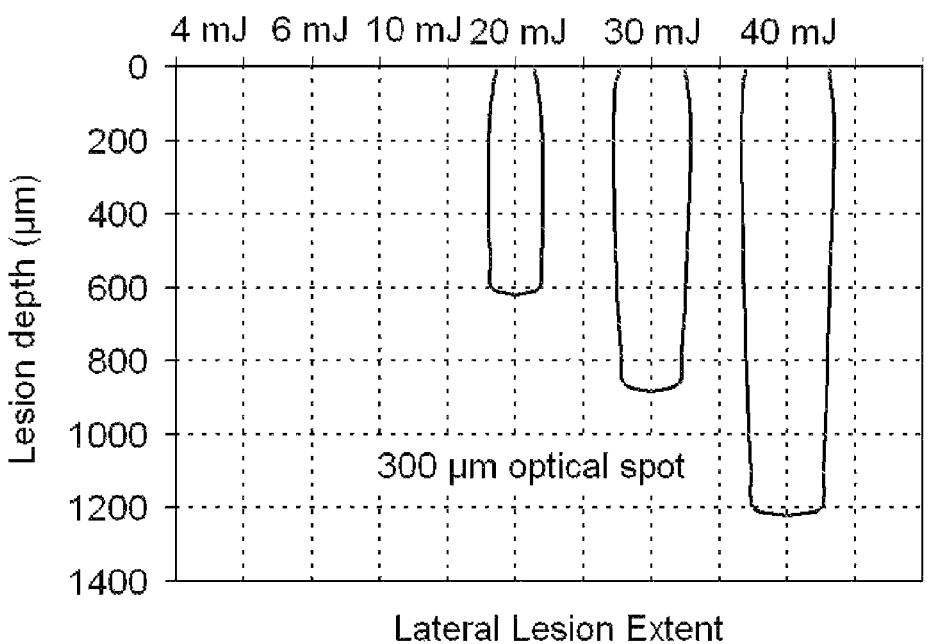
Figure 8G:
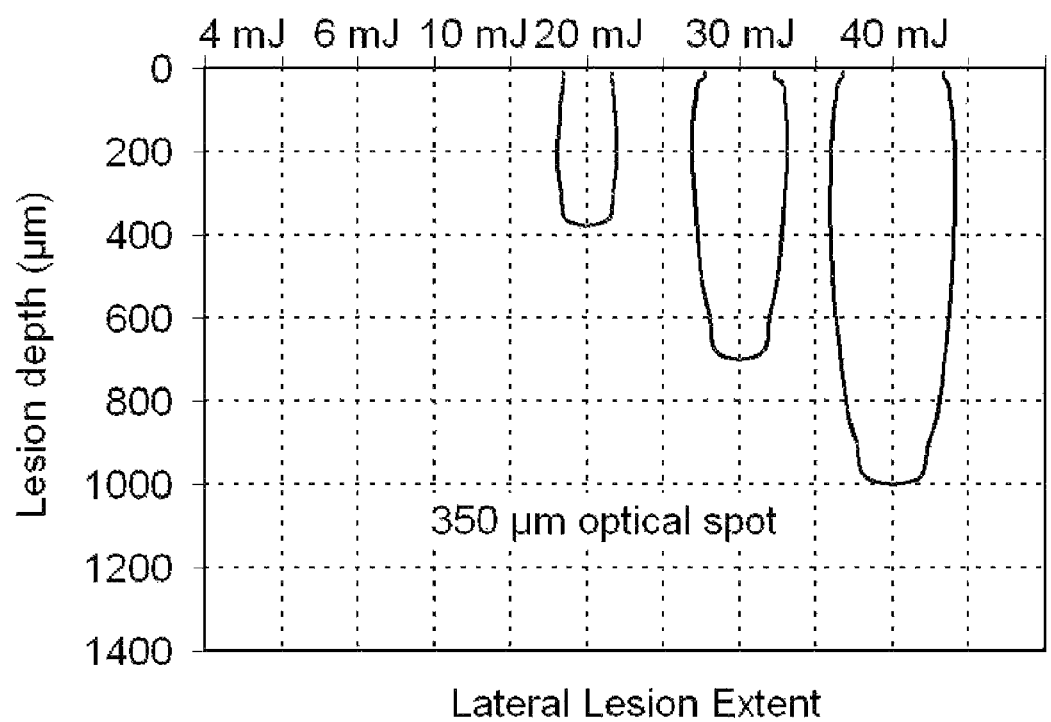

As can be seen from the results in FIGS. 7-9, the focus of the optical beam typically occurs at a depth that is significantly removed from the maximum depth of the representative lesion. For example, for pulse energies in the range of 35-40 mJ, the maximum depth in our study was achieved by a beam with a diameter at the skin surface of 260 µm, which corresponds to a focus depth of approximately 7 mm, even though the lesion only achieved a depth of approximately 1 mm. Thus, the inventive system can be significantly different from focusing systems that rely on focusing a beam at a selected depth in order to increase the optical intensity at or near the focus depth. In our case, the focus depth can be greater than 2 times the depth of the deepest portion of a typical lesion. Since the important factor is optical spot size, there is no upper bound on the depth of the focus. The optical beam can in fact be a collimated beam (i.e., practically infinite focus depth). The focus can also be outside of the tissue. In some aspects, the focus depth is about 2 to about 100 times the depth of the deepest portion of a typical lesion or about 5 to about 500 times the depth of the deepest portion of a typical lesion.

A laser system designer can efficiently use the expensive laser pulse energy that is available to increase the depth of lesions at a given pulse energy. In the example described by FIGS. 7-9, deep lesions were efficiently achieved at each selected pulse energy in the range of 3-40 mJ by choosing an optical spot size of the treatment beam at the skin surface of between 100 µm and 260 µm. As can be seen from FIG. 7, the optical spot size at the surface of the skin can be increased as pulse width is increased to increase the maximum depth of the representative lesions.

Figure 6:
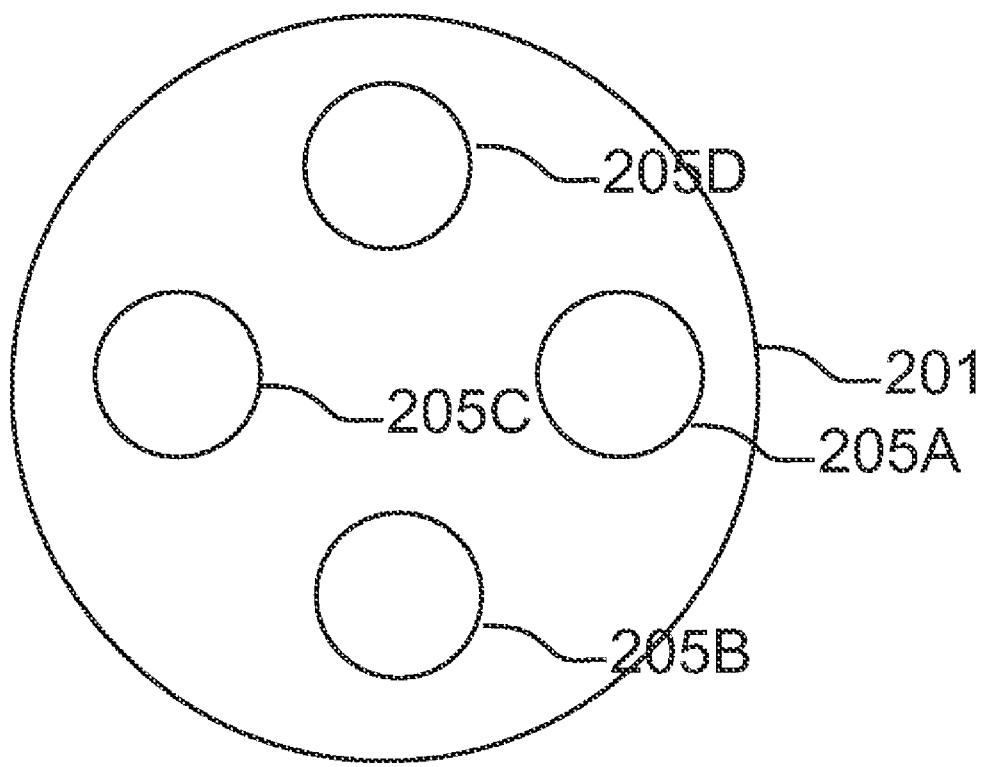
FIG. 6 is an illustration of an aspect of a fractional treatment system incorporating a rotating turret.

Other appropriate types of scanning devices can be used in this invention, such as for example, a galvanometer scanner, a piezo-electric scanner, and an acousto-optic scanner. Other appropriate types of beam adjustment devices can also be used, such as for example, other types of zoom lenses or a discretely adjustable lens variation system. One type of discretely adjustable lens variation system is illustrated in FIG. 6, which can be used to replace the adjustable lens group 123 of FIG. 1A. FIG. 6 depicts a rotating turret 201 containing discrete lenses 205A,B,C,D. Discrete lenses 205A-D may comprise a single element or a lens group. The rotating turret 205 or the adjustable lens group 123 can be manually adjusted or can be electronically adjusted, for example using a motor 182 that may optionally be controlled by a computer or other type of controller 180. The controller 180 can be accessed by the user through a user interface 184 to select appropriate treatment parameters. Through the user interface 184, the user can control the fractional optical treatment system (via the controller) to switch between a treatment mode that is semi-ablative and a treatment mode that is not semi-ablative. The controller 180 can also control parameters of the laser source such as the wavelength, pulse energy, pulse shape, pulse repetition rate, and pulse duration of an optical beam emitted from the laser source 140.

A combination of adjustment mechanisms can be incorporated for improved resolution or span. For example, FIGS. 2A-C illustrate an embodiment of the inventive apparatus that incorporates both an adjustable lens group 123 and a set of spacer tips 128A,B,C. The optical system used in FIG. 2A has a spacer tip 128A of a short length relative to the spacers used in FIGS. 2B (128B) and 2C (128C). To gain additional control over focus depth and spot size, the focus depth can be adjusted by adjusting the separation 110 between the output lens group 125 and the surface of the skin 199, where one or more beams is incident. The separation 110 can be adjusted simply, cheaply, and with no moving parts by using multiple spacer tips of different lengths that can be interchanged to achieve different focus depths. FIGS. 2A-2C are illustrations of the fractional treatment system of FIG. 1A-1C that depict the use of an adjustable zoom lens in combination with a set of spacers of different lengths. This combination can beneficially be used to increase the depth of focus beyond what would be easy to do given limited space or budget constraints for the optical design of the handpiece 100.

The inventive system can comprise a noncontact tip. A noncontact tip is a tip that is designed to be in contact with the skin, but that does not have a contact element in contact with the skin (either directly or indirectly through a substance, such as a gel that is applied to the skin) in a beam path of a laser treatment beam at the point where the laser beam enters the skin. Tips that are not noncontact may have, for example, a glass or sapphire plate in the laser beam path at the point that the contact plate touches the skin. For the high optical fluences used for semi-ablative fractional treatments, high fluence levels created near the skin surface may damage a contact plate. Furthermore, tissue that is removed from the skin surface may also attach to a contact plate and cause an absorption site that causes an increased rate of damage to the contact window. Damage to a contact window may obstruct the beam and so is typically undesirable.

The inventive system can comprise a contact tip. A contact tip is a tip that is configured such that a substantially transparent contact plate is in contact with the skin during treatment and the contact plate is in contact with the skin (either directly or indirectly through a substance, such as a gel that is applied to the skin) at the point where a laser treatment beam enters the skin. Contact treatment tips can be beneficial for treatment in the treatment modes that are not semi-ablative because they allow cooling to be delivered and/or because they can allow thermal heat spreading of the heat.

The inventive system can be sold with a set of tips that comprise one or more contact tips and one or more noncontact tips. For example, the inventive system can be sold with a set of tips that comprise a contact tip for treatments that are not semiablative and a noncontact tip for treatments that are semiablative. Whether a contact or noncontact tip is used will depend on the specific device configuration and the desired treatment outcome.

Although the detailed description contains many specifics, these should not be construed as limiting the scope of the invention but merely as illustrating different examples and aspects of the invention. It should be appreciated that the scope of the invention includes other embodiments not discussed in detail above. For example, reflective or diffractive optics may be used in place of the refractive optics described herein. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

In the claims, reference to an element in the singular is not intended to mean one and only one unless explicitly stated, but rather is meant to mean "one or more." In addition, it is not necessary for a device or method to address every problem that is solvable by different embodiments of the invention in order to be encompassed by the claims.

What is claimed is:

1. An apparatus for fractional dermatological treatment, the apparatus comprising:
a laser source configured to emit an optical beam at a laser wavelength in a range of 1350 nm to 2500 nm for which the absorption of the laser wavelength in water decreases as the tissue is heated from 30° C. to 80° C.; and
a fractional optical treatment system configured to deliver the optical beam to a target area of skin, said fractional optical treatment system comprising an adjustment mechanism that adjusts one or more parameters of the optical beam selected from the group consisting of a size of the optical beam at the skin surface, a focal depth of the optical beam below the skin surface, a numerical aperture of the optical beam as the optical beam enters the skin, and a beam cross-sectional shape at the skin surface in response to a preselected pulse energy for the optical beam.

2. The apparatus of claim 1 wherein the adjustment mechanism is configured to adjust the size of the optical beam at the skin surface.

3. The apparatus of claim 1 wherein the adjustment mechanism is configured to adjust the focal depth of the optical beam below the skin surface.

4. The apparatus of claim 1 wherein the adjustment mechanism is configured to adjust the numerical aperture of the optical beam as the optical beam enters the skin.

5. The apparatus of claim 1 wherein the adjustment mechanism is configured to adjust the beam cross-sectional shape at the skin surface.

6. The apparatus of claim 1 wherein the adjustment mechanism comprises an adjustable lens group.

7. The apparatus of claim 1 wherein the adjustment mechanism comprises a plurality of discretely interchangeable optical elements.

8. The apparatus of claim 1 wherein the laser source is configured to emit the optical beam with the laser wavelength in a range of about 1480 nm to about 1640 nm.

9. The apparatus of claim 1 wherein the laser wavelength is in a range of about 1560 nm to about 1640 nm.

10. The apparatus of claim 1 wherein the laser wavelength is about 1550 nm.

11. The apparatus of claim 1 wherein the laser wavelength is in a range of about 1380 nm to about 1420 nm.

12. The apparatus of claim 1 wherein the fractional optical treatment system includes a contact tip configured to be in contact with the skin during the fractional dermatological treatment.

* * * * *